(12) United States Patent
Hunn et al.

(10) Patent No.: US 7,513,891 B2
(45) Date of Patent: Apr. 7, 2009

(54) TEMPERATURE-SENSITIVE CANNULA

(75) Inventors: Marcel Hunn, Langenthal (CH);
Susanne Barkhahn, Bern (CH);
Andreas Reinmann, Luterbach (CH)

(73) Assignee: Disetronic Licensing AG, Burgdorf (CH)

( * ) Notice: Subject to any disclaimer, the term of this patent is extended or adjusted under 35 U.S.C. 154(b) by 0 days.

(21) Appl. No.: 11/183,270

(22) Filed: Jul. 15, 2005

(65) Prior Publication Data

US 2006/0030824 A1 Feb. 9, 2006

Related U.S. Application Data

(63) Continuation of application No. PCT/EP2004/000310, filed on Jan. 16, 2004.

(30) Foreign Application Priority Data

Feb. 13, 2003 (DE) ................. 103 06 013

(51) Int. Cl.
*A61M 5/00* (2006.01)
(52) U.S. Cl. ........................ 604/264; 604/523
(58) Field of Classification Search .............. 604/264, 604/531, 93.01, 272, 523–525
See application file for complete search history.

(56) References Cited

U.S. PATENT DOCUMENTS

| | | | |
|---|---|---|---|
| 2,828,744 A | 4/1958 | Hirsch et al. | |
| 3,830,239 A * | 8/1974 | Stumpf et al. | 606/25 |
| 3,986,506 A * | 10/1976 | Garber et al. | 604/406 |
| 4,022,215 A * | 5/1977 | Benson | 606/23 |
| 4,562,751 A | 1/1986 | Nason et al. | |
| 4,664,660 A * | 5/1987 | Goldberg et al. | 604/321 |
| 4,755,173 A | 7/1988 | Konopka et al. | |
| 4,790,817 A * | 12/1988 | Luther | 604/509 |
| 4,841,970 A * | 6/1989 | Rand | 607/113 |
| 4,976,704 A | 12/1990 | McLees | |
| 5,445,140 A * | 8/1995 | Tovey | 600/117 |
| 5,624,727 A * | 4/1997 | Stoy | 428/76 |
| 5,762,630 A * | 6/1998 | Bley et al. | 604/164.01 |
| 6,126,633 A | 10/2000 | Kaji et al. | |
| 6,616,680 B1 * | 9/2003 | Thielen | 606/200 |

FOREIGN PATENT DOCUMENTS

| | | |
|---|---|---|
| DE | 197 38 942 | 3/1999 |
| DE | 696 16 541 | 7/2002 |
| EP | 0 529 675 | 3/1993 |
| WO | WO 02/28458 | 10/2001 |

* cited by examiner

*Primary Examiner*—Nicholas D Lucchesi
*Assistant Examiner*—Theodore J Stigell
(74) *Attorney, Agent, or Firm*—Dorsey & Whitney LLP

(57) ABSTRACT

A cannula, for introduction into a body tissue, the cannula flexible after introduction, and rigid below a critical temperature and flexible above the critical temperature. In a method for the introduction of the cannula into the body tissue, the cannula is cooled to a temperature below the critical temperature and introduced into the body tissue. After being introduced, the cannula is brought to a temperature above the critical temperature by warming and thus becomes flexible.

10 Claims, 3 Drawing Sheets

TEMPERATURE-SENSITIVE CANNULA

CROSS-REFERENCE TO RELATED APPLICATION(S)

This application is a Continuation of International Patent Application PCT/EP2004/000310, filed on Jan. 16, 2004, which claims priority to Swiss Application No. 2003 0073/03, filed on Jan. 17, 2003, and German Application No. 103 06 013.8, filed on Feb. 13, 2003, the contents of which are incorporated in their entirety by reference herein.

BACKGROUND

The present invention relates to generally tube-like structures, e.g., conduits, needles, catheters, cannula, etc., their rigidity and flexibility, how to make and use them, and how to change and use their degree of rigidity or flexibility. More particularly, it relates to a cannula for insertion into body tissue, and to a method for inserting the cannula into the tissue. More particularly, the present invention relates to an infusion cannula of an infusion appliance.

In a great many therapeutic or diagnostic applications, uses or treatments, it is necessary for a cannula to be provided inside body tissue over quite a long period of time, for example in order to permit repeated or sustained administration of therapeutic or diagnostic fluids. In the treatment of patients with diabetes, for example, insulin from an infusion appliance is administered at regular intervals through a cannula which remains in the patient's body tissue over a period of several days.

For this purpose, it is known from U.S. Pat. No. 4,562,751, for example, to use a steel cannula. A steel cannula does have a simple structure, but it also has various disadvantages. The sharp needle tip of the rigid cannula can cause constant irritation of the surrounding tissue since it cannot adapt to movements of the tissue. Such a rigid cannula, when inserted, is uncomfortable for the patient or even painful. There is also a considerable risk of needlestick injuries when removing the needle-like cannula from the tissue.

Devices referred to as soft cannulas and which are flexible have therefore been developed. U.S. Pat. No. 4,755,173, for example, describes an injection set used for subcutaneous administration of a fluid, in which a steel needle is guided through a soft cannula so that the sharp tip of the steel needle protrudes from the soft cannula. With the aid of the steel needle, the soft cannula is inserted into body tissue. The steel needle is then removed from the soft cannula, as a result of which a fluid connection is established between the soft cannula and the tissue.

A soft cannula of this kind can easily follow the movements of the tissue, so that there is no irritation of the surrounding tissue. To insert the soft cannula, however, it is still necessary to use a rigid cannula, for example a steel cannula, which has to be removed after the soft cannula has been inserted. The soft cannula therefore also poses a risk of a needlestick injury. In addition, the opening through which the steel cannula has been removed has to be sealed off to permit correct use of the cannula. This procedure is complicated and increases the risk of a lack of leaktightness when fitting the cannula, for example in an infusion appliance.

SUMMARY

Objects of the present invention include to simplify the handling and structure of a cannula for insertion into body tissue, to reduce the number of individual parts needed for insertion, to improve the hygiene conditions when using such a cannula, and to reduce the risk of needlestick injuries when handling the cannula. In particular, a cannula is to be made available which can be inserted into body tissue without an additional rigid needle and which is soft and flexible in the inserted state. It is a further object of the invention to make available a method for inserting a cannula into body tissue, said method being easy to carry out and, in particular, requiring no additional rigid insertion aid.

The objects of the invention are addressed by providing a cannula for insertion into body tissue, which is flexible in the inserted state, wherein the cannula is rigid below a critical temperature range and is flexible above the critical temperature range, and by providing a method for inserting a cannula into body tissue, in which method, prior to insertion, the cannula is brought into a rigid state by cooling it to a temperature below a critical temperature range, introducing or inserting the cannula in the rigid state into the body tissue, and bringing the cannula, in the inserted state (i.e., after it has been inserted), into a flexible state by warming it to a temperature above the critical temperature range. Additional advantages, features and embodiments of the cannula and method are described herein.

In one embodiment, the present invention comprises a cannula, for insertion into body tissue, which is flexible in the inserted state, wherein the cannula is rigid below a temperature range and is flexible above the temperature range. The temperature range, which also may be referred to as the critical temperature range or the temperature range which brings about or effects a change in a quality or property, can be selected, narrowed or widened depending on the materials used in the present invention, e.g., the material used to form or make the cannula, its wall or a portion thereof, the medium received in or adjacent to the cannula and/or its wall, etc.

In one embodiment, the present invention comprises a cannula, for introduction into a body tissue, the cannula flexible after introduction, and rigid below a critical temperature and flexible above the critical temperature. The present invention encompasses a method for the introduction of the cannula into the body tissue comprising the steps of cooling the cannular to a temperature below the critical temperature and introducing it into the body tissue. After being introduced, the cannula is brought to a temperature above the critical temperature by warming and thus becomes flexible.

A cannula according to the present invention, which is used for insertion into body tissue and which is flexible in the inserted state, is designed in such a way that it is rigid below a critical temperature range and is flexible above the critical temperature range. In this sense, the cannula according to the invention is of a temperature-sensitive design, i.e. the cannula is in a rigid state at temperatures below the critical temperature range, so that it can penetrate and be inserted into body tissue, and it is in a flexible, soft state at a temperature above the critical temperature range, and it assumes this state, after insertion into the body tissue, by warming to a temperature above the critical temperature range so that it can follow movements of the tissue. In one embodiment, the critical temperature range lies advantageously in the range of body temperature, i.e. around 37° C. Ideally, in some preferred embodiments, the critical temperature range may involve an infinitesimally small range. However, during insertion into the body tissue, in order to ensure that the cannula maintains a rigid state until complete insertion, it is preferred that the cannula for insertion of the needle has a temperature markedly below such an infinitesimally small temperature range, that is to say, for example, markedly below 37° C.

In one embodiment of the method according to the present invention the cannula, prior to insertion, is brought into a rigid state by cooling it to a temperature below the critical temperature range. In the rigid state, the cannula is inserted into the body tissue and, by warming to a temperature above the critical temperature range, is brought into a flexible state. The cannula is in this case advantageously warmed by the tissue that surrounds it, which tissue generally has a temperature of 37° C. or above.

The cooling of the cannula preferably takes place by evaporation of a volatile medium which, for example, is applied to the cannula in the form of a cooling spray or disinfecting spray. Such a cooling spray or disinfecting spray also has the advantage of disinfecting and locally numbing the surface of the tissue before insertion of the cannula and of reducing the elasticity of the surface, i.e. of the skin. Such a medium can, for example, also be present as a breakable ampoule or as a capsule. Of course, it is also possible to cool the cannula by pre-cooling in a refrigerator compartment, for example by storing the cannula in an icebox before it is used.

According to the invention, the cannula is made of a material which is very rigid at temperatures below 37° C., so that a tissue surface can be penetrated without the use of an additional insertion aid. Plastic is preferably used for this purpose. Inside the tissue, which in humans, for example, has a temperature above 37° C., the material behaves as a flexible tube.

In a preferred embodiment, the cannula can be made of porous material, and a temperature-sensitive medium, preferably a liquid, can be received by the porous material. Honeycomb-shaped chambers are preferably formed for this purpose in the porous material. A liquid is chosen whose freezing point is below 37° C. By lowering the temperature of the liquid, the latter is frozen in the honeycomb-shaped chambers, as a result of which the flexural strength of the cannula increases and it is able to penetrate tissue. Within the tissue, the liquid inside the honeycomb-shaped chambers of the cannula thaws, with the result that the cannula is soft and flexible once more.

According to a further preferred embodiment of the invention, the cannula comprises a tube and a sleeve surrounding the tube, and said tube and said sleeve can be made, for example, from a material such as PTFE, PUR or SR. The tube is of a thin-walled configuration, such that it is flexible. The sleeve is likewise flexible and is preferably made from a plastic with a high degree of thermal expansion. Between the tube and the sleeve, a clearance space is formed which is preferably filled with a temperature-sensitive medium. It is advantageous if the interior of the tube, i.e. the channel for a therapeutic or diagnostic fluid, is also filled with the temperature-sensitive medium. A suitable temperature-sensitive medium is, for example, water or a saline solution. When a cannula of this kind is treated with a cooling spray, the temperature of the temperature-sensitive medium drops below the critical temperature range, i.e. the water in the clearance space between the tube and the sleeve and the channel freezes, with the result that the cannula becomes rigid. The stiffening of the cannula is assisted by the fact that the sleeve with the high degree of thermal expansion contracts below the critical temperature range. At lower temperatures, the overall structure of tube, sleeve and temperature-sensitive medium is thus rigid enough to allow tissue to be penetrated. It is also advantageous, in this case, to provide a support material in the clearance space between the tube and the sleeve. A suitable support material is, for example, a fibrous material such as carbon fibers or glass fibers. The fibers in the clearance space are arranged substantially in the longitudinal direction of the cannula so that, when the clearance space narrows through contraction of the sleeve, they can additionally contribute to the stiffening of the cannula.

The clearance space can be closed off. However, this is not absolutely essential since, even when the clearance space is not closed off, the temperature-sensitive medium remains in said space on account of capillary forces, for example. It is also conceivable for no temperature-sensitive medium to be provided inside the cannula if the thermal expansion properties or behavior of the materials are able to guarantee sufficient rigidity.

According to a further embodiment, the cannula comprises a tube surrounded by an absorbent material, for example PUR foam or PTFE (sintered), or by a support material. It is advantageous in this case to combine the absorbent material with the support material. As support material, it is possible, as has been described above, to use metal fibers, carbon fibers or glass fibers. In this initial state, i.e. at temperatures above the critical temperature range, the cannula is flexible. Before inserting the cannula into the body tissue, the cannula is dipped into a temperature-sensitive medium, such as a saline solution or water, and the absorbent material is completely saturated with the medium. By cooling the whole cannula to a temperature below the critical temperature range, the temperature-sensitive medium freezes, with the result that the cannula becomes rigid and is able to penetrate tissue. Inside the tissue, the temperature of the temperature-sensitive medium rises above the critical temperature range so that the medium thaws and the cannula is once again flexible. In this connection, it is possible that the temperature-sensitive medium may pass into the body tissue, so that, when selecting such a medium, care must be taken to ensure that it is biocompatible.

In a further embodiment, the cannula according to the invention is formed by a tube with a temperature-sensitive medium or a support material received in its wall. For this purpose, the material of the tube can be provided, for example, with a multiplicity of elongate chambers which are oriented in the longitudinal direction of the cannula. The chambers can then be filled with the support material or with the temperature-sensitive medium. According to a particularly preferred configuration of the cannula, a minimal play, i.e. a small clearance space, remains between the wall surface of an elongate chamber and the support material when the cannula is at a temperature above the critical temperature range. By means of this play, the tube of the cannula is soft and flexible. At temperatures below the critical temperature range, the material of the tube contracts so that the play between the wall surfaces and the support material is annulled and the cannula is rigid.

In the described embodiments of the cannula according to the invention, it is also possible, at a distal end of the cannula, to provide a stiffening part preferably forming a tip of the cannula. Such a stiffening part can, for example, be formed by a metal or ceramic tip. The stiffening part does of course form a solid and hard component inside the tissue, but, compared to a steel cannula which is rigid along its entire length, this stiffening part is extremely small, with the result that it causes hardly any irritation of the tissue.

In a cannula according to the present invention, no additional insertion aid is needed for inserting it into body tissue. It is therefore also unnecessary to take added measures for sealing after such an insertion aid has been removed. The properties of a cannula according to the invention can be achieved through the choice of a suitable material for the cannula or through the particular structure of the cannula. By means of the method according to the invention, a cannula can be inserted quickly and easily into body tissue. Also, some use and insertion method steps coincide with typical steps of traditional or typical cannula use and insertion, for example disinfecting the body tissue and cooling the cannula of the present invention, and some steps of traditional or typical use are omitted, for example removal of an insertion aid and sealing after the latter has been removed. It is therefore made much easier for the patient to insert and to wear a cannula needed for treatment or examination.

DETAILED DESCRIPTION

Figure 1:
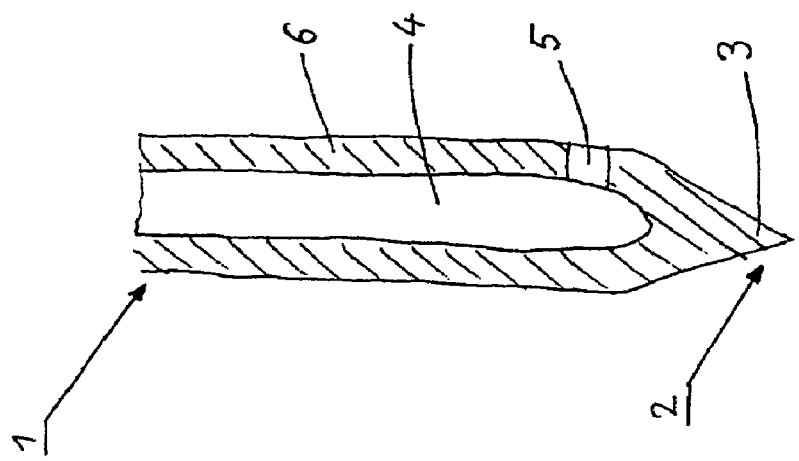
FIG. 1 is a longitudinal section through one embodiment of a cannula according to the present invention made from a temperature-sensitive material.

The front portion of a cannula 1 is shown in FIG. 1. The rear part (not shown) of the cannula 1 is, for example, secured on a cannula support in such a way that a fluid connection to a user appliance is established for conveying a therapeutic or diagnostic fluid into the cannula. At the distal end 2 of the cannula, which end is inserted into body tissue, the cannula is formed as a tip 3. To establish a fluid connection from the user appliance into body tissue, the cannula 1 has a channel 4 and, before the distal end 2, an opening 5 on the side of the cannula 1. A therapeutic or diagnostic fluid can then pass from the user appliance, through the channel 4 and the opening 5 and into the body tissue when the cannula is inserted into the tissue.

In the embodiment of the cannula according to the invention shown in FIG. 1, the material forming the cannula wall 6, which surrounds the channel 4, and forming the cannula tip 3 is a temperature-sensitive material. Thus, according to the invention, the material is rigid at temperatures below a critical temperature range and is flexible at temperatures above the critical temperature range. In the rigid state, i.e. at lower temperatures, the cannula can be inserted into body tissue. The temperature-sensitive material of the cannula warms inside the body tissue, with the result that the cannula is brought or moved into a flexible state. A temperature-sensitive material of this kind is formed, for example, from a plastic such as soft PVC.

Figure 2:
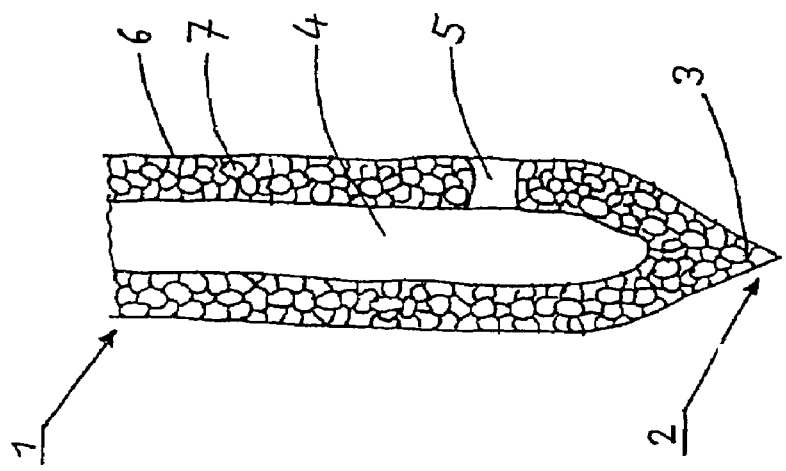
FIG. 2 is a longitudinal section through a second embodiment of a cannula according to the invention made from a porous material.

FIG. 2 shows a second embodiment of a cannula according to the invention in which the cannula wall 6 and the cannula tip 3 are formed homogeneously from a porous material. Near the distal end 2 of the cannula 1, the cannula wall 6 is provided with an opening 5 through which a fluid can pass from the channel 4 of the cannula 1 into body tissue. In the embodiment shown, the porous material has honeycomb-shaped chambers 7 which are filled with a liquid whose freezing point lies below 37° C. By cooling the cannula 1 made of porous material with the chambers 7, the cannula is brought into a rigid state and can be inserted into the tissue.

Figure 3:
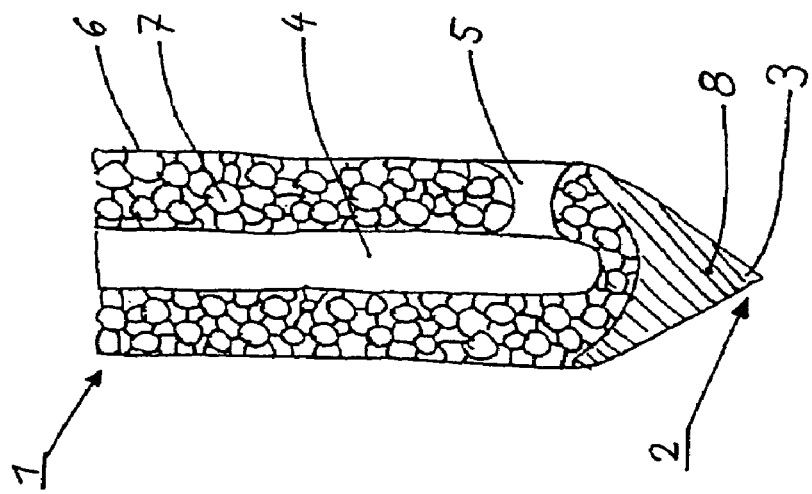
FIG. 3 is a longitudinal section through another embodiment of a cannula according to the invention, with a stiffening part at the distal end.

FIG. 3 shows another embodiment of a cannula according to the present invention which in principle corresponds to the structure of the cannula from FIG. 2 but, at its distal end 2, has a stiffening part 8 acting as cannula tip. The stiffening part can be a metal or ceramic tip. The stiffening part 8 facilitates penetration of the surface of the tissue. In the procedure of inserting the cannula, the act of puncturing the surface of the tissue requires the greatest force, so that the cannula is subjected to the most stress at this stage. However, the cannula's complete penetration, following the puncturing stage, can also be facilitated by the stiffening part.

Figure 5:
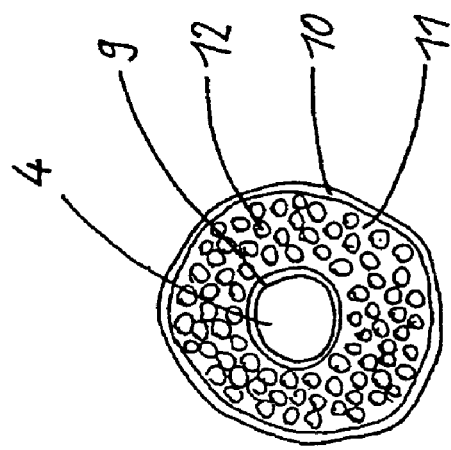
FIG. 5 is a cross section through the cannula from FIG. 4.
Figure 4:
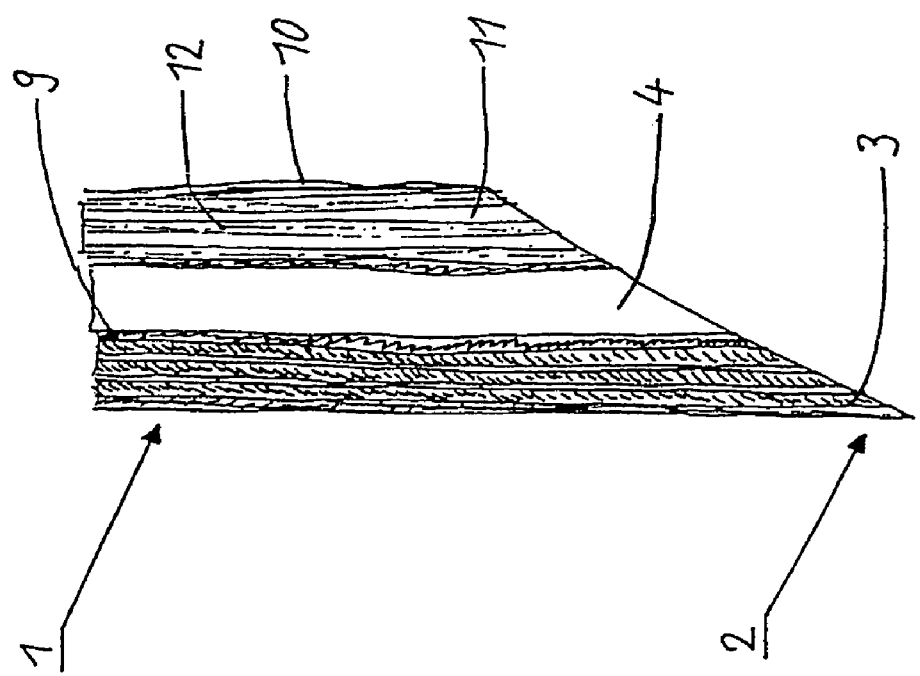
FIG. 4 is a longitudinal section through a fourth embodiment of a cannula according to the invention, with a tube and a sleeve.

FIG. 4 shows a fourth embodiment of a cannula according to the invention which is formed from a thin-walled tube 9 and from a sleeve 10 surrounding the tube 9. Between the tube 9 and the sleeve 10, a clearance space 11 is formed which is filled with carbon fibers, glass fibers or metal fibers as support material 12. The distal end area 2 of the cannula 1 is formed by an oblique cut through the tube 9 and the sleeve 10, so that a tip 3 is formed on one circumferential side of the cannula. In this embodiment, the channel 4 opens in the longitudinal direction of the cannula 1 directly into body tissue. FIG. 5 shows a cross section through the embodiment from FIG. 4. It will be clear from this that the carbon fibers 12 are arranged next to one another in the longitudinal direction of the cannula in the circumferential direction inside the clearance space 11. The sleeve 10 is made of plastic with a high degree of thermal expansion. When the cannula 1 cools, the sleeve 10 contracts, whereupon the clearance space 11 between the tube 9 and the sleeve 10 narrows and the carbon fibers 12 lie tightly packed against one another, with the result that the cannula becomes rigid. In addition, in the flexible state of the cannula 1, it is possible to provide a temperature-sensitive medium in the clearance space 11 between the carbon fibers 12 and in the channel 4. The temperature-sensitive medium freezes when the cannula cools and in so doing it additionally contributes to the stiffening of the cannula.

Figure 6:
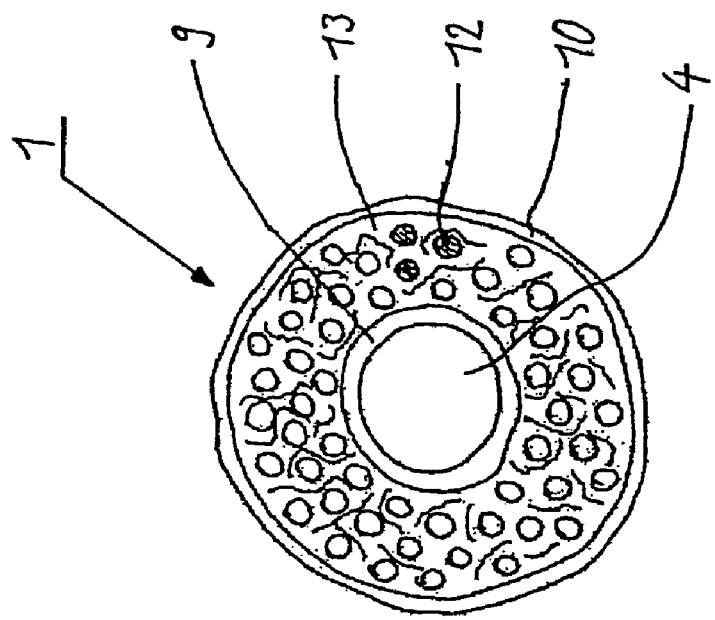
FIG. 6 is a cross section through another embodiment of a cannula according to the invention, with an absorbent material.

In a fifth embodiment of the cannula according to the invention as shown in FIG. 6, the tube 9 is surrounded by an absorbent material 13 through which a support material 12, for example in the form of carbon fibers, runs in the longitudinal direction. In FIG. 6, the tube 9 and the absorbent material 13 with the support material 12 are surrounded by a sleeve 10. The sleeve 10 is, however, not absolutely essential for a cannula according to the invention. Before insertion into body tissue, a cannula of this embodiment is dipped into a temperature-sensitive fluid so that the absorbent material is completely saturated with the fluid. The cannula is then cooled, so that the fluid inside the absorbent material 13 freezes and thus stiffens the cannula. The support material 12 is held securely inside the absorbent material 13 and supports the stiffening of the cannula.

Figure 7:
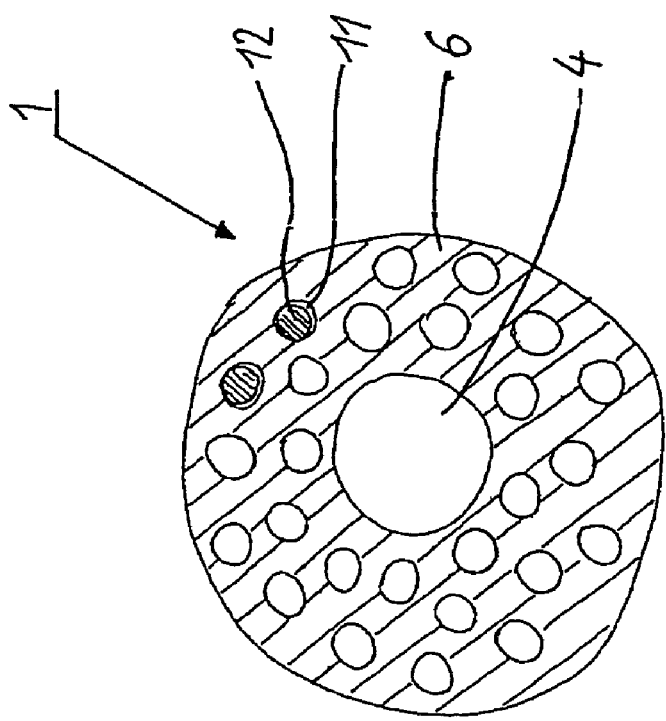
FIG. 7 is a cross section through another embodiment of the cannula according to the invention, with a support material in a wall of the cannula.

FIG. 7 shows another embodiment of a cannula according to the invention in which the cannula wall 6 is designed as a flexible tube. A multiplicity of elongate openings 14 running in the longitudinal direction of the cannula are provided inside the wall 6. A support material 12 is arranged inside the elongate openings 14, the cross-hatching in the figure indicating, by way of example, two upper openings. Between the support material 12 and the wall surface of the elongate openings 14, a clearance space 15 is left when the cannula is at a temperature above the critical temperature range. In this state, the cannula is soft and flexible since the clearance space permits play for movements of the tube 6. When the temperature of the cannula is dropped to a range below the critical temperature range, the material of the cannula wall 6 contracts. In doing this, the surface of the elongate openings 14 comes to lie on the support material 12, so that the clearance space 15 disappears. The material of the cannula wall 6 bears firmly on the support material 12. In this state, the cannula 1 is rigid and can be inserted into body tissue. There, the temperature rises again to above the critical temperature range, with the result that the cannula becomes soft and flexible again.

The invention has been described by way of example on the basis of the embodiments shown. However, it is possible to combine the individual features of the embodiments or to effect further modifications without departing from the scope of the invention. Further, while exemplary embodiments, including preferred embodiments, of the present invention have been described herein, it is contemplated that various modifications could be made without deviating from the spirit of the present invention. For example, the material selected for providing a cannula in accordance with the present invention can be selected based on its or a desired response or change of state in response to a selected temperature or a selected temperature range. Also, the structure of a cannula in accordance with the present invention may be varied, along with the liquid or substance received therein, to select a desired temperature range. Accordingly, the scope of the present invention is to be ascertained by the appended claims.

The invention claimed is:

1. A method for inserting a cannula into body tissue, comprising the steps of:
   providing the cannula, wherein the cannula comprises a porous material, in which a temperature-sensitive medium is received,
   causing the cannula to be rigid prior to inserting the cannula by cooling the cannula to a temperature below a freezing point of the temperature-sensitive medium,
   inserting the cannula while rigid into the body tissue, and
   after inserting the cannula, causing the cannula to be flexible by warming the cannula to a temperature above the freezing point and in a body temperature range.

2. The method as claimed in claim 1, wherein the cannula is cooled by evaporation of a volatile medium from the cannula.

3. The method as claimed in claim 1, wherein the cannula is cooled by pre-cooling in a refrigerator compartment.

4. The method as claimed in claim 1, wherein, after insertion, the cannula is warmed by the body tissue.

5. The method as claimed in claim 1, wherein the temperature-sensitive medium is a liquid at body temperature range and has a freezing point at or below 0° C.

6. The method as claimed in claim 1, wherein the temperature-sensitive medium is water.

7. The method as claimed in claim 1, wherein the temperature-sensitive medium is saline solution.

8. The method as claimed in claim 1, wherein the temperature-sensitive medium is biocompatible with body tissue.

9. A method for inserting a cannula comprising a tapered tip and a cannula portion into body tissue, comprising the steps of:
   providing the cannula, wherein the cannula comprises a porous material, in which a temperature-sensitive medium is received,
   causing the cannula to be rigid prior to inserting the cannula by cooling the cannula to a temperature below a freezing point of the temperature-sensitive medium,
   inserting the cannula while rigid into the body tissue beginning with said tapered tip, and
   after inserting the cannula, causing the cannula to be flexible, such that the temperature-sensitive medium thaws, by warming the cannula to a temperature above the freezing point and in a body temperature range.

10. A method for inserting a cannula into body tissue, comprising the steps of:
    providing the cannula while above a critical temperature range, wherein the cannula is flexible above the critical temperature range and rigid below a critical temperature range,
    causing the cannula to be rigid prior to inserting the cannula by cooling the cannula below the critical temperature range by evaporation of a volatile medium from the cannula, wherein said volatile medium is applied to said cannula in the form of one of a cooling spray and a disinfecting spray;
    inserting the cannula while rigid into the body tissue, and
    after inserting the cannula, causing the cannula to be flexible by warming the cannula above the critical temperature range and in a body temperature range.

* * * * *

UNITED STATES PATENT AND TRADEMARK OFFICE
CERTIFICATE OF CORRECTION

PATENT NO. : 7,513,891 B2  Page 1 of 1
APPLICATION NO. : 11/183270
DATED : April 7, 2009
INVENTOR(S) : Marcel Hunn et al.

It is certified that error appears in the above-identified patent and that said Letters Patent is hereby corrected as shown below:

PTO  Should Read
On the Title page, after item [30]: After "Feb. 13, 2003 (DE) 103 06 013" insert --Jan 17, 2003 (CH) 0073/03--

Signed and Sealed this

Eighteenth Day of August, 2009

David J. Kappos
*Director of the United States Patent and Trademark Office*